United States Patent [19]

Goi et al.

[11] 4,387,238

[45] Jun. 7, 1983

[54] EPOXYSUCCINAMIC ACID COMPOUNDS

[75] Inventors: Masami Goi, Ageo; Kazuya Kameo, Abiko; Jiro Sawada, Kodaira; Kazunori Hanada; Masaharu Tamai, both of Ageo; Kiyoshi Oguma, Kitamoto, all of Japan

[73] Assignee: Taisho Pharmaceutical Co., Ltd., Tokyo, Japan

[21] Appl. No.: 263,586

[22] Filed: May 14, 1981

Related U.S. Application Data

[63] Continuation of Ser. No. 80,211, Oct. 1, 1979, abandoned.

[30] Foreign Application Priority Data

Sep. 30, 1978 [JP]  Japan .................................. 53-121026

[51] Int. Cl.$^3$ .................. C07D 303/48; C07D 407/12; C07D 409/12; C07D 405/12; C07D 405/10; C07D 413/06; C07D 405/06
[52] U.S. Cl. ..................................... 549/549; 549/473; 549/60; 544/374; 544/147; 544/58.7; 546/268; 546/159; 546/171; 546/207; 548/517; 424/278; 424/275; 424/285; 424/263; 424/258; 424/250; 424/248.55; 424/246; 424/274; 424/267
[58] Field of Search ............. 260/348.46, 347.3, 347.4, 260/326.36; 549/60, 549, 473; 546/265, 268, 171, 207, 159; 544/58.7, 147, 374; 548/517

[56] References Cited

U.S. PATENT DOCUMENTS 3,911,111 10/1975 Sawada et al. ...................... 424/118
4,064,241 12/1977 Ross et al. ........................ 260/348.46
4,091,221  5/1978 Carr et al. ....................... 260/348.46

FOREIGN PATENT DOCUMENTS 2809036  9/1978  Fed. Rep. of Germany .

OTHER PUBLICATIONS

S. M. Creighton et al., Canadian Journal of Chemistry, vol. 45, (1967), pp. 1304–1306.
Edward B. Roche, Design of Biopharmaceutical Properties Through Prodrugs and Analogs, (1977), pp. 346–347.
Chemical Abstracts, vol. 87, 202108y; 85238c; 202125b; 68129a; 68128z.
K. Hanada et al., Agric. Biol. Chem., vol. 42(3), pp. 523–528, 529–536, 537–541 (1978).
C & En., Aug. 18, 1975, p. 27.

*Primary Examiner*—Norma S. Milestone
*Attorney, Agent, or Firm*—Kenway & Jenney

[57] ABSTRACT

The epoxysuccinamic acid compounds of the present invention are prepared by reaction of monoesters of epoxysuccinic acid or monoesters of epoxysuccinic acid chloride with amino compounds. These epoxysuccinamic acid compounds have excellent anti-inflammatory activity, thiol protease inhibitory activity, muscular dystrophy inhibitory activity and anti-hypertensive activity without acceleration of vascular permeability.

3 Claims, No Drawings

EPOXYSUCCINAMIC ACID COMPOUNDS

This is a continuation of application Ser. No. 080,211, filed Oct. 1, 1979, now abandoned.

BACKGROUND

Prior to the present invention, there have been known E-64 (U.S. Pat. No. 3,911,111), its intermediates [Chemical Abstracts, 87, 202108y (1977), ibid., 87, 85238c (1977), ibid., 87, 202125b (1977) and ibid. 87, 68128z (1977)], and epoxysuccinic acid derivatives having acyl or amino acid moieties attached to their carbonyl groups (German Patent Application Laying Open No. P 28 09 036) prepared by several of the present inventors.

The novel epoxysuccinamic acid compounds of the present invention are distinguished from the known compounds as described above by their excellent anti-inflammatory activity.

DESCRIPTION AND PREFERRED EMBODIMENTS

The present invention relates to a novel epoxysuccinamic acid compound of the formula

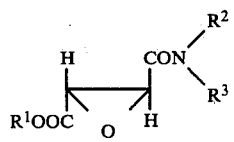

(I)

wherein $R^1$ is hydrogen, alkali metal, alkyl having 1-5 carbon atoms, alkenyl having 2-4 carbon atoms, alkynyl having 2-4 carbon atoms, phenyl, benzyl, cycloalkyl having 5-6 carbon atoms, cycloalkenyl having 5-6 carbon atoms, cycloalkenemethyl having 6-7 carbon atoms, or alkyl having 1-3 carbon atoms substituted with cycloalkyl having 5-6 carbon atoms, $R^2$ is hydrogen or alkyl having 1-5 carbon atoms and $R^3$ is phenyl, benzyl, furfuryl, thenyl, pyridyl, quinolinyl, cycloalkanemethyl having 4-7 carbon atoms, or phenyl substituted with 1-3 members selected from the group consisting of halogen, methyl, trifluoromethyl, methoxy, acetyl, hydroxy and nitro, or $R^2$ and $R^3$ taken together with the nitrogen atom to which they are attached form a 5-6 membered heterocyclic ring of pyrrolidino, piperidino, piperazino, morpholino or thiamorpholino, or the 5-6 membered heterocyclic ring substituted with methyl.

These epoxysuccinamic acid compounds of the present invention have excellent anti-inflammatory, thiol protease inhibitory, muscular dystrophy inhibitory and anti-hypertensive activity without acceleration of vascular permeability.

In the present specification and claims, unless otherwise noted, the term "alkyl" refers to both straight and branched chain alkyl groups, the term "halogen" refers to chloro, bromo, iodo and fluoro, and both epoxysuccinamic acid compounds and epoxysuccinic acid compounds are limited to the trans isomers, namely, the two carbonyl groups on the oxirane ring are in the trans configuration.

With regard to the compounds of the present invention, the substituent on the alkyl in $R^1$ may be on any position. The substituent on the phenyl in $R^2$ or $R^3$ may be on any position, and when 2 or 3 substituents are present, they are the same or different. Examples of the 5-6 membered heterocyclic ring are pyrrolidino, piperidino, piperazino, morpholino, thiamorpholino and the like. The substituent on the 5-6 membered heterocyclic ring may be on any position.

A preferred group of compounds of the present invention is the compound of the formula (I) wherein $R^1$ is alkyl having 1-5 carbon atoms or cycloalkyl having 5-6 carbon atoms, $R^2$ is hydrogen, and $R^3$ is phenyl.

A compound of the formula (I) may be prepared, for example, as follows:

An epoxysuccinic acid monoester of the formula

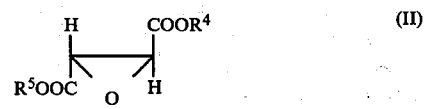

(II)

wherein $R^4$ is hydrogen or alkali metal, and $R^5$ is alkyl having 1-5 carbon atoms, alkenyl having 2-4 carbon atoms, alkynyl having 2-4 carbon atoms, phenyl, benzyl, cycloalkyl having 5-6 carbon atoms, cycloalkenyl having 5-6 carbon atoms, cycloalkenemethyl having 6-7 carbon atoms, or alkyl having 1-3 carbon atoms substituted with cycloalkyl having 5-6 carbon atoms, may be treated with a chlorinating agent such as oxalyl chloride, thionyl chloride or the like to give the corresponding acid chloride. To the acid chloride, an amino compound of the formula

(III)

wherein $R^2$ and $R^3$ are as defined above, may be added dropwise under ice cooling to give the compound of formula (I) wherein $R^1$ is $R^5$. In this reaction, the amino compound may be accompanied by a base such as triethylamine, pyridine, methylmorphorine or the like.

Alternatively, the compound of formula (II) wherein $R^4$ is hydrogen may be reacted with the amino compound of the formula (III) in the presence of a condensing agent such as N,N'-dicyclohexylcarbodiimide, 1-ethyl-3-(3-dimethylaminopropyl)carbodiimide or the like to give the compound of the formula (I) wherein $R^1$ is $R^5$. It is desirable to carry out the reaction in the presence of a N-hydroxy compound such as N-hydroxysuccinimide, 1-hydroxybenzotriazole or the like. The resulting epoxysuccinamate may be dissolved in a suitable alcohol such as methanol, ethanol, propanol, isopropanol, cyclohexanemethanol or the like, and then may be allowed to transesterize in the presence of a catalyst such as sulfuric acid, an alkali metal alcoholate or an alkali hydroxide to give another epoxysuccinamate.

The compound of formula (I) wherein $R^1$ is $R^5$ may be treated with an alkali hydroxide such as sodium hydroxide, potassium hydroxide or the like, and then, if necessary, followed by addition of an organic solvent such as ethanol, acetone, ether or the like to precipitate an alkali metal salt of the epoxysuccinamic acid, i.e., the compound of the formula (I) wherein $R^1$ is an alkali metal cation.

The salt thus obtained may be acidified with an inorganic acid such as hydrochloric acid or sulfuric acid, or an organic acid such as formic acid or acetic acid, and then extracted with a suitable organic solvent such as ethyl acetate, ether, benzene or chloroform to give the compound of formula (I) wherein $R^1$ is hydrogen.

The compounds of formula (II) can be prepared by the method as described in German Patent Application Laying Open No. P 28 09 036 or by that with some modification, and the compound of formula (III) are to a large extent commercially available.

The compounds of the present invention show excellent anti-inflammatory activity as measured by their ability to inhibit adjuvant induced polyarthritis as compared with the known epoxysuccinates. That is, they show potent and continuous effectiveness on oral administration of smaller components than the known epoxysuccinic acid compounds. Effect of the compounds of the present invention on the development of adjuvant-induced polyarthritis in rat was assayed as follows: Adjuvant arthritis is produced by a single intracutaneous injection of 0.1 ml of the adjuvant mixture containing heat-killed mycobacteria of the human Aoyama B strain suspended in liquid paraffin in 0.6% in the middle part of the distal tail of Sprague Dawley rat (female, 8 weeks old). The compounds suspended in 0.5% carboxymethylcellulose solution protect the animal against the development of lession of adjuvant arthritis in daily oral administration beginning on the day of adjuvant injection and continuing for 24 days thereafter. The activity is measured as the mean inhibition percent for the increase of the hind paw volume of the 8 rats/group on the days 17 and 23 on which the legs become inflamed and reach maximum volumes. The results are shown in Table 1. The compound Nos. in Table 1 are as defined in Examples as described hereinafter.

TABLE 1

| Compound No. | Dose(mg/kg of body weight) | Inhibition(%) 17 days | Inhibition(%) 23 days |
|---|---|---|---|
| 1 | 30 | 70 | 62 |
| 5 | 30 | 65 | 48 |
| 25 | 30 | 76 | 58 |
| 31 | 30 | 45 | 38 |
| 40 | 30 | 40 | 35 |
| 45 | 30 | 65 | 49 |
| 48 | 30 | 45 | 40 |
| 66 | 30 | 75 | 62 |
| 76 | 30 | 48 | 42 |
| 98 | 30 | 55 | 41 |

The compounds of the present invention also inhibit effectively and specifically thiol proteases such as papain, bromelains and some kinds of cathepsin in which some sulfhydryl groups are essential for activity. On the other hand, the compounds of the present invention have no inhibitory activity against proteolysis of casein by trypsin, chymotrypsin, pepsin, acid protease of Peacilomyces carioti and Nagarse (trademark of Nagase Industry), esterolysis of benzoylarginine ethyl ester by kallikrein, fibrinolysis by human plasmin.

Papain inhibitory activity of the compounds of the present invention was assayed as follows: To 0.5 ml of a solution of papain (80 μg/ml, Sigma Chem. Co., 2x, cry.), were added 0.25 ml of 40 mM cysteine dissolved in 20 mM disodium ethylenediamine tetraacetic acid solution adjusted pH to 6.8 with sodium hydroxide and 0.25 ml of 33 mM phosphate buffer (pH 6.8) with or without inhibitor. After incubation for 15 minutes at 40° C., the resulting mixture was added to 5 ml of 1% milk casein solution in the same buffer as described above, and further incubated for 10 minutes at 40° C. Then the mixture was mixed with 5 ml of 0.44 M trichloroacetic acid solution and followed by filtration with a sheet of Toyo filter paper No. 4.

The extinction of the filtrate was read at 280 nm. The percent inhibition was calculated from the formula, $100 \times (B-A)/B$; wherein B stands for the absorbance without inhibitor and A for the absorbance with inhibitor. The amount of inhibitor for 50% inhibition was expressed as $ID_{50}$, and shown in Table 2. The compound Nos. in Table 2 are as defined in Examples as described hereinafter.

TABLE 2

| Compound No. | $ID_{50}(\gamma)$ | Compound No. | $ID_{50}(\gamma)$ |
|---|---|---|---|
| 1 | 24.04 | 34 | 32.35 |
| 2 | 40.30 | 35 | 16.52 |
| 3 | 34.72 | 36 | 4.04 |
| 4 | 138.88 | 37 | 5.81 |
| 5 | 22.32 | 38 | 4.26 |
| 6 | 25.51 | 39 | 3.08 |
| 7 | 105.93 | 40 | 13.20 |
| 8 | 208.33 | 41 | 15.23 |
| 9 | 120.19 | 42 | 14.15 |
| 10 | 32.05 | 43 | 3.01 |
| 11 | 25.05 | 44 | 3.14 |
| 12 | 20.16 | 45 | 5.89 |
| 13 | 13.30 | 46 | 2.98 |
| 14 | 67.57 | 47 | 3.64 |
| 15 | 26.04 | 48 | 3.83 |
| 16 | 22.73 | 49 | 3.94 |
| 17 | 28.41 | 50 | 16.95 |
| 18 | 22.36 | 51 | 18.66 |
| 19 | 20.83 | 52 | 5.32 |
| 20 | 20.49 | 53 | 1.63 |
| 21 | 93.28 | 54 | 10.07 |
| 22 | 95.01 | 55 | 3.14 |
| 23 | 868.05 | 56 | 148.80 |
| 24 | 3.47 | 57 | 46.30 |
| 25 | 3.68 | 58 | 231.50 |
| 26 | 2.08 | 59 | 154.50 |
| 27 | 3.05 | 60 | 32.35 |
| 28 | 6.41 | 61 | 19.65 |
| 29 | 2.91 | 62 | 6.16 |
| 30 | 3.68 | 63 | 4.23 |
| 31 | 53.19 | 64 | 8.32 |
| 32 | 71.40 | 65 | 13.65 |
| 33 | 95.10 | 66 | 11.05 |
| 67 | 5.14 | 88 | 118.41 |
| 68 | 24.04 | 89 | 14.81 |
| 69 | 12.05 | 90 | 50.25 |
| 70 | 90.25 | 91 | 9.68 |
| 71 | 4.13 | 92 | 120.10 |
| 72 | 146.51 | 93 | 21.55 |
| 73 | 128.50 | 94 | 1.51 |
| 74 | 39.62 | 95 | 0.330 |
| 75 | 130.10 | 96 | 0.158 |
| 76 | 79.53 | 97 | 0.266 |
| 77 | 145.21 | 98 | 0.205 |
| 78 | 34.23 | 99 | 0.104 |
| 79 | 36.25 | 100 | 0.231 |
| 80 | 120.53 | 101 | 4.05 |
| 81 | 36.76 | 102 | 1.34 |
| 82 | 277.80 | 103 | 13.42 |
| 83 | 130.20 | 104 | 0.315 |
| 84 | 12.65 | 105 | 0.278 |
| 85 | 39.50 | 106 | 0.301 |
| 86 | 105.50 | 107 | 0.214 |
| 87 | 98.10 | 108 | 0.234 |

The pharmaceutical forms contemplated by the present invention include pharmaceutical compositions suited for oral, parenteral, and rectal use, e.g., tablets, powder packets, cachets, dragees, capsules, solutions, suspensions, sterile injectable forms, suppositories, bougies, and the like. The carrier employed may be, for example, either a solid or liquid. Examples of solid carriers are lactose, terra alba, sucrosem talc, gelatin, agar, pectin, acacia, magnesium stearate, stearic acid and the like. Examples of liquid carriers are syrup, peanut oil, olive oil, water and the like. Similarly, the carrier or diluent can include any time delay material well known to the art, such as glyceryl monostearate or glyceryl distearate alone or with a wax.

The compounds of the present invention can be used as anti-inflammatory agents in dosages of 5–400 mg/kg, preferably 10–50 mg/kg in oral or injectable preparations as described above, to protect mammals against the development of arthritis.

The compounds of the present invention are of extremely low toxicity. That is, they show hardly any oral acute toxicity on mice at dosages less than 2 g/kg of body weight. Moreover, no side effect is observed after administration of 1 g/kg/day orally to 30 days for laboratory animals.

The following examples illustrate the present invention.

EXAMPLE 1

To a suspension of monoethyl potassium epoxysuccinate (1.7 g) in ethyl ether (30 ml), oxalyl chloride (1.2 g) in ethyl ether was added dropwise with stirring under ice-cooling and the mixture was stirred for an hour at room temperature. To the reaction mixture, aniline (1.6 g) in ethyl ether was added dropwise with stirring under ice-cooling, and the mixture was stirred at room temperature for an hour. The precipitate produced was filtered off and the filtrate was washed with a saturated aqueous sodium chloride solution, dried over magnesium sulfate and concentrated to dryness. The crude product was purified by chromatography using silica gel as an absorbent and benzene as an eluent, and then recrystallized from n-hexane-acetone to give 1.0 g of ethyl N-phenyl-2,3-epoxysuccinamate (Compound No. 1). m.p. 83°–84° C.

EXAMPLE 2

Following the procedure of Example 1, monoethyl potassium epoxysuccinate (1.0 g) was successively treated with oxalyl chloride (0.75 g) and m-trifluoromethylaniline (1.63 g) to give 0.64 g of ethyl N-3'-trifluoromethylphenyl-2,3-epoxysuccinamate (Compound No. 2) as colorless needles melting at 71°–74° C.

EXAMPLE 3

Following the procedure of Example 1, monoethyl potassium epoxysuccinate (1.0 g) was successively treated with oxalyl chloride (0.75 g) and m-acetylaniline (1.29 g) to give 0.72 g of ethyl N-3'-acetylphenyl-2,3-epoxysuccinamate (Compound No. 3) as colorless powder melting at 105°–108° C.

EXAMPLE 4

Following the procedure of Example 1, monoethyl potassium epoxysuccinate (1.0 g) was successively treated with oxalyl chloride (0.75 g) and o-hydroxyaniline (1.04 g) to give 0.53 g of ethyl N-2'-hydroxyphenyl-2,3-epoxysuccinamate (Compound No. 4) as colorless flakes melting at 157°–159° C.

EXAMPLE 5

Following the procedure of Example 1, monoethyl potassium epoxysuccinate (0.99 g) was successively treated with oxalyl chloride (0.7 g) and p-nitroaniline (1.39 g) to give 0.7 g of ethyl N-4'-nitrophenyl-2,3-epoxysuccinamate (Compound No. 5) as colorless needles melting at 172°–172.5° C.

EXAMPLE 6

Following the procedure of Example 1, monoethyl potassium epoxysuccinate (0.99 g) was successively treated with oxalyl chloride (0.7 g) and p-bromoaniline (1.72 g) to give 0.4 g of ethyl N-4'-bromophenyl-2,3-epoxysuccinamate (Compound No. 6) as colorless needles melting at 139°–140° C.

EXAMPLE 7

Following the procedure of Example 1, monoethyl potassium epoxysuccinate (1.58 g) was successively treated with oxalyl chloride (1.1 g) and ethyl α-aminobenzoate (2.67 g) to give 1.0 g of ethyl N-2'-carboethoxyphenyl-2,3-epoxysuccinamate (Compound No. 7) as colorless needles melting at 83°–84° C.

EXAMPLE 8

Following the procedure of Example 1, monoethyl potassium epoxysuccinate (1.0 g) was successively treated with oxalyl chloride (0.75 g) and 2,6-dichloroaniline (1.63 g) to give 1.1 g of ethyl N-2',6'-dichlorophenyl-2,3-epoxysuccinamate (Compound No. 8) as colorless needles melting at 154.5°–156° C.

EXAMPLE 9

Following the procedure of Example 1, monoethyl potassium epoxysuccinate (0.99 g) was successively treated with oxalyl chloride (0.7 g) and 2,4,6-tribromoaniline (3.6 g) to give 0.4 g of ethyl N-2',4',6'-tribromophenyl-2,3-epoxysuccinamate (Compound No. 9) as colorless plates melting at 167°–168° C.

EXAMPLE 10

Following the procedure of Example 1, monoethyl potassium epoxysuccinate (1.0 g) was successively treated with oxalyl chloride (0.75 g) and m-fluoro aniline (1.12 g) to give 0.52 g of ethyl N-3'-fluorophenyl-2,3-epoxysuccinamate (Compound No. 10) as colorless needles melting at 55.5°–60° C.

EXAMPLE 11

Following the procedure of Example 1, monoethyl potassium epoxysuccinate (0.99 g) was successively treated with oxalyl chloride (0.7 g) and α-aminopyridine (1.1 g) to give 0.2 g of ethyl N-2'-pyridinyl-2,3-epoxysuccinamate (Compound No. 11) as colorless needles melting at 90°–91° C.

EXAMPLE 12

Following the procedure of Example 1, monoethyl potassium epoxysuccinate (1.0 g) was successively treated with oxalyl chloride (0.75 g) and 8-aminoquinoline (1.46 g) to give 0.71 g of ethyl N-8'-quinolinyl-2,3-epoxysuccinamate (Compound No. 12) as colorless needles melting at 107°–108.5° C.

EXAMPLE 13

Following the procedure of Example 1, monoethyl potassium epoxysuccinate (1.0 g) was successively treated with oxalyl chloride (0.75 g) and benzylamine (1.02 g) to give 0.54 g of ethyl N-benzyl-2,3-epoxysuccinamate (Compound No. 13) as colorless needles melting at 90°–91° C.

EXAMPLE 14

Following the procedure of Example 1, monoethyl potassium epoxysuccinate (1.0 g) was successively treated with oxalyl chloride (0.75 g) and furfurylamine (0.98 g) to give 0.57 g of ethyl N-furfuryl-2,3-epoxysuccinamate (Compound No. 14) as colorless needles melting at 72°-73° C.

EXAMPLE 15

Following the procedure of Example 1, monoethyl potassium epoxysuccinate (1.0 g) was successively treated with oxalyl chloride (0.75 g) and phenethylamine (1.3 g) to give 0.72 g of ethyl N-phenethyl-2,3-epoxysuccinamate (Compound No. 15) as colorless needles melting at 80°-82° C.

EXAMPLE 16

Following the procedure of Example 1, monoethyl potassium epoxysuccinate (1.98 g) was successively treated with oxalyl chloride (1.5 g) and n-propylamine (1.2 g) to give 1.5 g of ethyl N-propyl-2,3-epoxysuccinamate (Compound No. 16) as colorless needles melting at 58° C.

EXAMPLE 17

Following the procedure of Example 1, monoethyl potassium epoxysuccinate (1.5 g) was successively treated with oxalyl chloride (1.04 g) and isoamylamine (2.3 g) to give 0.9 g of ethyl N-isoamyl-2,3-epoxysuccinamate (Compound No. 17) as colorless needles melting at 59°-61° C.

EXAMPLE 18

Following the procedure of Example 1, monoethyl potassium epoxysuccinate (1.0 g) was successively treated with oxalyl chloride (0.75 g) and cyclopentylamine (0.86 g) to give 0.71 g of ethyl N-cyclopentyl-2,3-epoxysuccinamate (Compound No. 18) as colorless needles melting at 94°-97° C.

EXAMPLE 19

Following the procedure of Example 1, monoethyl potassium epoxysuccinate (5 g) was successively treated with oxalyl chloride (3.72 g) and cyclohexylamine (5 g) to give 3.5 g of ethyl N-cyclohexyl-2,3-epoxysuccinamate (Compound No. 19) as colorless needles melting at 98°-100° C.

EXAMPLE 20

Following the procedure of Example 1, monoethyl potassium epoxysuccinate (1.0 g) was successively treated with oxalyl chloride (0.75 g) and cyclohexanemethylamine (1.07 g) to give 0.5 g of ethyl N-cyclohexanemethyl-2,3-epoxysuccinamate (Compound No. 20) as colorless needles melting at 90°-91° C.

EXAMPLE 21

Following the procedure of Example 1, monoethyl potassium epoxysuccinate (1.65 g) was successively treated with oxalyl chloride (1.15 g) and morpholine (1.44 g) to give 0.4 g of ethyl N-oxydiethylene-2,3-succinamate (Compound No. 21) as colorless plates melting at 102° C.

EXAMPLE 22

Following the procedure of Example 1, monoethyl potassium epoxysuccinate (1.98 g) was successively treated with oxalyl chloride (1.26 g) and thiamorpholine (2.06 g) to give 0.51 g of ethyl N-thiadiethylene-2,3-epoxysuccinamate (Compound No. 22) as colorless needles melting at 125°-127° C.

EXAMPLE 23

Following the procedure of Example 1, monoethyl potassium epoxysuccinate (1.49 g) was successively treated with oxalyl chloride (1.04 g) and N-methylpiperazine (1.8 g) to give 1.25 g of ethyl N-N'-methylaminodiethylene-2,3-epoxysuccinamate (Compound No. 23) as colorless plates melting at 82°-83° C.

EXAMPLE 24

Following the procedure of Example 1, monocyclopentyl potassium epoxysuccinate (0.73 g) was successively treated with oxalyl chloride (0.6 g) and p-iodoaniline (1.34 g) to give 0.42 g of cyclopentyl N-4'-iodophenyl-2,3-epoxysuccinamate (Compound No. 24) as colorless needles melting at 109°-111° C.

EXAMPLE 25

Following the procedure of Example 1, monocyclopentyl potassium epoxysuccinate (5.0 g) was successively treated with oxalyl chloride (2.55 g) and cyclohexylamine (3.96 g) to give 2.5 g of cyclopentyl N-cyclohexyl-2,3-epoxysuccinamate (Compound No. 25) as colorless needles melting at 93°-97° C.

EXAMPLE 26

Following the procedure of Example 1, mono 2-cyclopentylethyl potassium epoxysuccinate (2.66 g) was successively treated with oxalyl chloride (1.26 g) and aniline (1.86 g) to give 1.74 g of 2'-cyclopentylethyl N-phenyl-2,3-epoxysuccinamate (Compound No. 26) as colorless needles melting at 97°-101° C.

EXAMPLE 27

Following the procedure of Example 1, mono 3-cyclohexylpropyl potassium epoxysuccinate (2.94 g) was successively treated with oxalyl chloride (1.26 g) and aniline (1.86 g) to give 1.41 g of 3'-cyclohexylpropyl N-phenyl-2,3-epoxysuccinamate (Compound No. 27) as colorless needles melting at 103°-105° C.

EXAMPLE 28

Following the procedure of Example 1, monophenyl potassium epoxysuccinate (3.64 g) was successively treated with oxalyl chloride (2.10 g) and aniline (1.4 g) to give 0.82 g of phenyl N-phenyl-2,3-epoxysuccinamate (Compound No. 28) as colorless needles melting at 121° C.

EXAMPLE 29

Following the procedure of Example 1, monobenzyl potassium epoxysuccinate (1.0 g) was successively treated with oxalyl chloride (0.49 g) and o-methoxyaniline (0.95 g) to give 0.32 g of benzyl N-2'-methoxyphenyl-2,3-epoxysuccinamate (Compound No. 29) as colorless needles melting at 76°-78° C.

EXAMPLE 30

Following the procedure of Example 1, monoallyl potassium epoxysuccinate (2.1 g) was successively treated with oxalyl chloride (1.26 g) and aniline (1.86 g) to give 1.24 g of allyl N-phenyl-2,3-epoxysuccinamate (Compound No. 30) as colorless needles melting at 32° C.

EXAMPLE 31

Following the procedure of Example 1, monoethyl potassium epoxysuccinate (1.0 g) was successively treated with oxalyl chloride (0.75 g) and N-methylcyclohexylamine (1.15 g) to give 0.64 g of ethyl N-methyl-N-cyclohexyl-2,3-epoxysuccinamate (Compound No. 31) as colorless needles melting at 52°–55° C.

EXAMPLE 32

Following the procedure of Example 1, monoethyl potassium epoxysuccinate (1.0 g) was successively treated with oxalyl chloride (0.75 g) and N-methylcyclohexanemethylamine (1.3 g) to give 0.81 g of ethyl N-methyl-N-cyclohexanemethyl-2,3-epoxysuccinamate (Compound No. 32) as colorless needles melting at 60°–61° C.

EXAMPLE 33

Following the procedure of Example 1, monoethyl potassium epoxysuccinate (1.0 g) was successively treated with oxalyl chloride (0.75 g) and 2-methylmorpholine (1.1 g) to give 0.74 g of ethyl N-1'-methyloxydiethylene-2,3-epoxysuccinamate (Compound No. 33) as colorless needles melting at 105°–107° C.

Following the procedure of Example 1 using the corresponding starting materials, there were obtained the following epoxysuccinamaic acid compounds, respectively.

Methyl N-isopropyl-2,3-epoxysuccinamate (Compound No. 34)
Methyl N-2'-methylphenyl-2,3-epoxysuccinamate (Compound No. 35)
Propyl N-4'-iodophenyl-2,3-epoxysuccinamate (Compound No. 36)
Isopropyl N-2'-methoxyphenyl-2,3-epoxysuccinamate (Compound No. 37)
Allyl N-cyclopentanemethyl-2,3-epoxysuccinamate (Compound No. 33)
Isobutyl N-furfuryl-2,3-epoxysuccinamate (Compound No. 39)
Isobutyl N-phenyl-2,3-epoxysuccinamate (Compound No. 40)
2'-Butynyl N-ethyl-2,3-epoxysuccinamate (Compound No. 41)
2'-Butynyl N-thenyl-2,3-epoxysuccinamate (Compound No. 42)
Isoamyl N-phenyl-2,3-epoxysuccinamate (Compound No. 43)
Cyclohexyl N-cyclohexyl-2,3-epoxysuccinamate (Compound No. 44)
Cyclohexyl N-phenyl-2,3-epoxysuccinamate (Compound No. 45)
2'-Cyclopentenyl N-phenyl-2,3-epoxysuccinamate (Compound No. 46)
Phenyl N-cyclopentyl-2,3-epoxysuccinamate (Compound No. 47)
Phenyl N-benzyl-2,3-epoxysuccinamate (Compound No. 48)
Benzyl N-3'-fluorophenyl-2,3-epoxysuccinamate (Compound No. 49)

EXAMPLE 34

To a suspension of monomethyl potassium epoxysuccinate (1.0 g) in ethyl ether (30 ml), oxalyl chloride (0.75 g) in ethyl ether was added dropwise with stirring under ice-cooling and the mixture was stirred for an hour at room temperature. To the reaction mixture, aniline (1.02 g) in ethyl ether was added dropwise with stirring under ice-cooling, and the mixture was stirred for an additional hour at room temperature. The precipitate produced was filtered off and the filtrate was washed with a saturated aqueous sodium chloride solution, dried over magnesium sulfate and concentrated to dryness. The crude product was purified by chromatography using silica gel as an absorbent and benzene as an eluent to give 0.84 g of methyl N-phenyl-2,3-epoxysuccinamate (Compound No. 50) as colorless oil.

MS m/e: 221 (M+).
IR $\nu_{max}^{neat}$ cm$^{-1}$: 3300, 1755, 1685.
NMR (CDCl$_3$) $\delta$=3.57, 3.73 (2H, d,d,J=2H$_z$) 3.76 (3H, s), 7.00-7.60 (5H, m), 7.65 (1H, b.s., disappeared upon the treatment with heavy water).

Example 35

Following the procedure of Example 34, monoethyl potassium epoxysuccinate (1.0 g) was successively treated with oxalyl chloride (0.75 g) and m-toluidine (1.02 g) to give 0.75 g of ethyl N-3'-methylphenyl-2,3-epoxysuccinamate (Compound No. 51) as colorless oil.

MS m/e: 249 (M+).
IR $\nu_{max}^{neat}$ cm$^{-1}$: 3280, 1750, 1680.
NMR (CDCl$_3$) $\delta$=1.28 (3H, t, J=9H$_z$), 2.30 (3H, s), 3.55, 3.74 (2H, d,d, J=2H$_z$), 4.24 (2H, q, J=9H$_z$), 6.76-7.44 (4H, m), 7.75 (1H, b.s., disappeared upon the treatment with heavy water).

EXAMPLE 36

Following the procedure of Example 34, mono-n-butyl potassium epoxysuccinate (1.06 g) was successively treated with oxalyl chloride (0.63 g) and aniline (1.03 g) to give 0.61 g of butyl N-phenyl-2,3-epoxysuccinamate (Compound No. 52) as colorless oil.

MS m/e: 263 (M+).
IR $\nu_{max}^{neat}$ cm$^{-1}$: 3320, 1745, 1680.
NMR (CDCl$_3$) $\delta$=0.9 (3H, t, J=9.0 H$_z$), 1.52 (4H, m), 3.56, 3.73 (2H, d,d, J=2.0 H$_z$), 4.15 (2H, t, J=9.0 H$_z$), 7.26 (5H, m), 7.76 (1H, b.s., disappeared upon the treatment with heavy water).

EXAMPLE 37

Following the procedure of Example 34, mono 3'-cyclohexenemethyl potassium epoxysuccinate (0.843 g) was successively treated with oxalyl chloride (0.45 g) and aniline (0.6 g) to give 0.53 g of 3'-cyclohexenemethyl N-phenyl-2,3-epoxysuccinamate (Compound No. 53) as colorless oil.

MS m/e: 301 (M+).
IR $\nu_{max}^{neat}$ cm$^{-1}$: 3320, 1750, 1690.
NMR (CDCl$_3$) $\delta$=1.60-2.40 (7H, b.s.), 3.61, 3.79 (2H, d,d, J=2.0 H$_z$), 3.64 (2H, s), 5.60 (2H, s), 7.00-7.60 (5H, m), 7.70 (1H, b.s., disappeared upon the treatment of heavy water).

EXAMPLE 38

Following the procedure of Example 34, mono methyl potassium epoxysuccinate (1.84 g) was successively treated with oxalyl chloride (0.75 g) and monoethylamine (0.9 g) to give 0.72 g of methyl N-ethyl-2,3-epoxysuccinamate (Compound No. 54) as colorless oil.

MS m/e: 173 (M+).
IR $\nu_{max}^{neat}$ cm$^{-1}$: 3320, 1750, 1680.
NMR (CDCl$_3$) $\delta$=1.10 (3H, t, J=6.0 H$_z$), 3.02 (2H, q, J=6.0 H$_z$), 3.60, 3.78 (2H, d,d, J=2.0 H$_z$), 3.88 (3H, s).

EXAMPLE 39

Following the procedure of Example 34, monoethyl potassium epoxysuccinate (1.0 g) was successively treated with oxalyl chloride (0.75 g) and a 28% aqueous ammonia solution (1.5 ml) to give 0.27 g of ethyl 2,3-epoxysuccinamate (Compound No. 55) as colorless oil.

MS m/e: 159 (M+).

IR $\nu_{max}^{neat}$ cm$^{-1}$: 3310, 3225, 1750, 1680.

NMR (CDCl$_3$) δ=1.28 (3H, t, J=9.0 Hz), 3.54, 3.73 (2H, d,d, J=2.0 Hz), 4.25 (2H, q, J=9.0 Hz), 7.73 (2H, b.s., disappeared upon the treatment with heavy water).

EXAMPLE 40

Following the procedure of Example 34, monoethyl potassium epoxysuccinate (1.0 g) was successively treated with oxalyl chloride (0.75 g) and diisobutylamine (1.3 g) to give 0.81 g of ethyl N,N-diisobutyl-2,3-epoxysuccinamate (Compound No. 56) as colorless oil.

MS m/e: 271 (M+).

IR $\nu_{max}^{neat}$ cm$^{-1}$: 1755, 1655.

NMR (CDCl$_3$) δ=0.7-1.1 (14H, m), 1.28 (3H, t, J=9.0 Hz), 2.84-3.50 (4H, m), 3.63, 3.77 (2H, d,d, J=2.0 Hz), 4.22 (2H, q, J=9.0 Hz).

EXAMPLE 41

Following the procedure of Example 34, monoethyl potassium epoxysuccinate (1.0 g) was successively treated with oxalyl chloride (0.75 g) and diethylamine (0.74 g) to give 0.68 g of ethyl N,N-diethyl-2,3-epoxysuccinamate (Compound No. 57) as colorless oil.

MS m/e: 215 (M+).

IR $\nu_{max}^{neat}$ cm$^{-1}$: 1755, 1655.

NMR (CDCl$_3$) δ=1.12, 1.24 (6H, t,t, J=9.0 Hz), 1.29 (3H, t, J=9.0 Hz), 3.38, 3.44 (4H, q,q, J=9.0 Hz), 3.65, 3.76 (2H, d,d, J=2.0 Hz), 4.22 (2H, q, J=9.0 Hz).

EXAMPLE 42

Following the procedure of Example 34, monoethyl potassium epoxysuccinate (1.0 g) was successively treated with oxalyl chloride (0.75 g) and N-methylbenzylamine (1.3 g) to give 0.61 g ethyl N-methyl-N-benzyl-2,3-epoxysuccinamate (Compound No. 58) as colorless oil.

MS m/e: 263 (M+).

IR $\nu_{max}^{neat}$ cm$^{-1}$: 1750, 1655.

NMR (CDCl$_3$) δ=1.29 (3H, t, J=9.0 Hz), 2.90 (2H, s), 3.00 (3H, s), 3.68, 3.84 (2H, d,d, J=2.0 Hz), 4.20 (2H, q, J=9.0 Hz), 7.18 (5H, s).

EXAMPLE 43

Following the procedure of Example 34, monoethyl potassium epoxysuccinate (1.0 g) was successively treated with oxalyl chloride (0.75 g) and N-propylaniline (1.4 g) to give 0.78 g of ethyl N-propyl-N-phenyl-2,3-epoxysuccinamate (Compound No. 59) as colorless oil.

MS m/e: 277 (M+).

IR $\nu_{max}^{neat}$ cm$^{-1}$: 1755, 1675.

NMR (CDCl$_3$) δ=0.88 (3H, t, J=9.0 Hz), 1.18 (3H, t, J=9.0 Hz), 1.55 (2H, m), 3.27, 3.68 (2H, d,d, J=2.0 Hz), 3,69 (2H, t, J=7.0 Hz), 4.11 (2H, q, J=9.0 Hz), 7.33 (5H, b.s.).

Following the procedure of Example 34 using the corresponding starting materials, there were obtained the following epoxysuccinamic acid compounds, respectively.

Methyl N-isopropyl-2,3-epoxysuccinamate (Compound No. 60)
Methyl N-cyclohexyl-2,3-epoxysuccinamate (Compound No. 61)
Propyl N-phenyl-2,3-epoxysuccinamate (Compound No. 62)
Propyl N-cyclopentyl-2,3-epoxysuccinamate (Compound No. 63)
Propyl N-isopropyl-2,3-epoxysuccinamate (Compound No. 64)
Isopropyl N-ethyl-2,3-epoxysuccinamate (Compound No. 65)
Cyclohexyl N-ethyl-2,3-epoxysuccinamate (Compound No. 66)
Benzyl N-isopropyl-2,3-epoxysuccinamate (Compound No. 67)

EXAMPLE 44

To a suspension of monoethyl potassium epoxysuccinate (0.77 g) in ethyl ether (30 ml), oxalyl chloride (0.75 g) in ethyl ether was added dropwise with stirring under ice-cooling and the mixture was stirred for an hour at room temperature. To the resulting mixture, a solution of N-carbobenzoxy 1,4-diaminobutane (1.1 g) and triethylamine (0.48 g) in ethyl ether was added dropwise with stirring under ice-cooling, and the mixture was stirred for an additional hour at room temperature. The resulting precipitate was filtered off and the filtrate was washed with a saturated aqueous sodium chloride solution, dried over magnesium sulfate and concentrated to dryness. The residue was purified by silica gel column chromatography using benzene as a developer. The crude crystals thus obtained were recrystallized from acetone-n-hexane to give 0.97 g of ethyl N-carbobenzoxyaminobutyl-2,3-epoxysuccinamate (Compound No. 68) as colorless plates melting at 94°-95° C.

EXAMPLE 45

Following the procedure of Example 44, monoethyl potassium epoxysuccinate (0.77 g) was successively treated with oxalyl chloride (0.75 g) and a mixture of N-carbonbenzoxy 1,5-diaminopentane (1.2 g) and triethylamine (0.48 g) to give 1.06 g of ethyl N-carbobenzoxyaminopentyl-2,3-epoxysuccinamate (Compound No. 69) as colorless granules melting at 53°-54° C.

Following the procedure of Example 44, there were obtained the following epoxysuccinamic acid compounds.

Methyl N-oxydiethylene-2,3-epoxysuccinamate (Compound No. 70)
Allyl N-phenethyl-2,3-epoxysuccinamate (Compound No. 71)
Cyclopentanemethyl N-N'-methylaminodiethylene-2,3-epoxysuccinamate (Compound No. 72)

EXAMPLE 46

To a suspension of monoethyl potassium epoxysuccinate (1.98 g) in ethyl ether (30 ml), oxalyl chloride (1.5 g) in ethyl ether was added dropwise with stirring under ice-cooling and the mixture was stirred for an additional hour at room temperature. To the reaction mixture, a solution of pyrrolidine (0.72 g) and triethylamine (1.1 g) in ethyl ether was added dropwise with stirring under ice-cooling and the mixture was stirred for an hour at room temperature. The precipitate produced was filtered off and the filtrate was washed with a saturated aqueous solution of sodium chloride, dried over magnesium sulfate and concentrated to dryness. The residue was purified by silica gel column chromatography using benzene as a developer to give 1.3 g of ethyl N-tetramethylene-2,3-epoxysuccinamate (Compound No. 73) as colorless oil.

MS m/e: 213 (M+).

IR $\nu_{max}^{neat}$ cm$^{-1}$: 1750, 1650.

NMR (CDCl$_3$) $\delta$=1.27 (3H, t,J=9.0 H$_z$), 1.65 (4H, b.s.), 3.49 (4H, b.s.), 3.68, 3.84 (2H, d,d, J=2.0 H$_z$), 4.25 (2H, q, J=9.0 H$_z$).

EXAMPLE 47

Following the procedure of Example 46, monopropargyl potassium epoxysuccinate (0.61 g) was successively treated with oxalyl chloride (0.37 g) and a mixture of piperidine (0.25 g) and triethylamine (0.3 g) to give 0.34 g of propargyl N-pentamethylene-2,3-epoxysuccinamate (Compound No. 74) as colorless oil.

MS m/e: 237 (M+).

IR $\nu_{max}^{neat}$ cm$^{-1}$: 3250, 2140, 1750, 1650.

NMR (CDCl$_3$) $\delta$=1.65 (6H, b.s.), 2.51 (1H, t, J=2.5 H$_z$), 3.50 (4H, b.s.), 3.68, 3.84 (2H, d,d, J=2.0 H$_z$), 4.71 (2H, d, J=2.5 H$_z$).

EXAMPLE 48

Following the procedure of Example 46, monoethyl potassium epoxysuccinate (1.0 g) was successively treated with oxalyl chloride (0.75 g) and a mixture of 2-methylpyrrolidine (0.5 g) and triethylamine (0.6 g) to give 0.51 g of ethyl N-1'-methyltetramethylene-2,3-epoxysuccinamate (Compound No. 75) as colorless oil.

MS m/e: 227 (M+).

IR $\nu_{max}^{neat}$ cm$^{-1}$: 1750, 1650.

NMR (CDCl$_3$) $\delta$=1.21 (3H, d, J=9.0 H$_z$), 1.29 (3H, t, J=9.0 H$_z$), 1.63 (4H, b.s.), 3.50 (3H, b.s.), 3.66, 3.85 (2H, d,d, J=2.0 H$_z$), 4.23 (2H, q, =9.0 H$_z$).

EXAMPLE 49

Following the procedure of Example 46, monoethyl potassium epoxysuccinate (1.0 g) was successively treated with oxalyl chloride (0.75 g) and a mixture of 4-methylpiperidine (0.44 g) and triethylamine (0.55 g) to give 0.68 g of ethyl N-3'-methylpentamethylene-2,3-epoxysuccinamate (Compound No. 76) as colorless oil.

MS m/e: 251 (M+).

IR $\nu_{max}^{neat}$ cm$^{-1}$: 1750, 1650.

NMR (CDCl$_3$) $\delta$=1.23 (3H, d, J=9.0 H$_z$), 1.28 (3H, t, J=9.0 H$_z$), 1.65 (5H, b.s.), 3.52 (4H, b.s.), 3.65, 3.82 (2H, d,d, J=2.0 H), 4.23 (2H, q. J=9.0 H$_z$).

Following the procedure of Example 46 using the corresponding starting materials, there were obtained the following epoxysuccinamic acid compounds, respectively.

Ethyl N-pentamethylene-2,3-epoxysuccinamate (Compound No. 77)
Benzyl N-pentamethylene-2,3-epoxysuccinamate (Compound No. 78)
3'-Cyclopentanepropyl N-tetramethylene-2,3-epoxysuccinamate (Compound No. 79)
Ethyl N-1'-methylthiadiethylene-2,3-epoxysuccinamate (Compound No. 80)

EXAMPLE 50

To a suspension of monoethyl potassium epoxysuccinate (1.98 g) in ethyl ether (30 ml), oxalyl chloride (1.5 g) in ethyl ether was added dropwise with stirring under ice-cooling, and the mixture was stirred for an hour at room temperature. To the reaction mixture, a solution of anthranilic acid (1.4 g) and triethylamine (7 g) in benzene was added with stirring under ice-cooling and the mixture was stirred for an additional hour at room temperature. The reaction mixture was made acidic (pH 2) with hydrochloric acid and extracted with benzene. The extract was washed with a saturated aqueous solution of sodium chloride, dried over magnesium sulfate and evaporated to dryness. The residue was purified by silica gel column chromatography using n-hexane-acetone as a developer and the resulting crude crystals were recrystallized from n-hexane-acetone to give 0.87 g of ethyl N-2'-carboxyphenyl-2,3-epoxysuccinamate (Compound No. 81) as colorless needles melting at 165° C.

EXAMPLE 51

Following the procedure of Example 50, monoethyl potassium epoxysuccinate (1.98 g) was successively treated with oxalyl chloride (1.5 g) and 4-chloroanthranilic acid (1.9 g) and triethylamine (7 g) to give 0.51 g of ethyl N-2'-carboxy-5'-chlorophenyl-2,3-epoxysuccinamte (Compound No. 82) as colorless needles melting at 179° C.

EXAMPLE 52

To a suspension of monoethyl potassium epoxysuccinate (1.0 g) in ethyl ether (30 ml), oxalyl chloride (0.75 g) in ethyl ether was added dropwise with stirring under ice-cooling, and the mixture was stirred for an hour at room temperature. To the reaction mixture, a solution of cyclopropanemethylamine hydrochloride (0.55 g) and pyridine (1.0 g) in ethyl ether was added dropwise with stirring under ice-cooling, and the mixture was stirred for an additional hour at room temperature. The precipitate produced was filtered off and the filtrate was washed with a saturated aqueous solution of sodium chloride, dried over magnesium sulfate and concentrated to dryness. The crude product thus obtained was purified by silica gel column chlomatography using benzene as a developer, and the resulting crude crystals were recrystallized from n-hexane-acetone to give 0.42 g of ethyl N-cyclopropanemethyl-2,3-epoxysuccinamate (Compound No. 83) as colorless needles melting at 50°-53° C.

EXAMPLE 53

To a suspension of monophenyl potassium epoxysuccinate (1.23 g) in ethyl ether (30 ml), oxalyl chloride (0.7 g) in ethyl ether was added dropwise with stirring under ice-cooling and the mixture was stirred for an hour at room temperature. To the reaction mixture, a solution of methylamine hydrochloride (0.5 g) and triethylamine (1.5 g) in ethyl ether was added dropwise with stirring under ice-cooling, and the mixture was stirred for an additional hour at room temperature. The precipitate produced was filtered off and the filtrate was washed with a saturated aqueous sodium chloride solution, dried over magnesium sulfate and concentrated to dryness. The residue was purified by silica gel column chromatography using benzene as a developer to give 0.48 g of phenyl N-methyl-2,3-epoxysuccinamate (Compound No. 84) as colorless oil.

MS m/e: 221 (M+).

IR $\nu_{max}^{neat}$ cm$^{-1}$: 3320, 1750, 1660.

NMR (CDCl$_3$) $\delta$=2.94 (3H, s), 3.59, 3.75 (2H, d,d, J=2.0 H$_z$), 7.10-7.60 (5H, m), 7.65 (1H, b.s., disappeared upon the treatment with heavy water).

EXAMPLE 54

Following the procedure of Example 53, monoethyl potassium epoxysuccinate (1.0 g) was successively treated with oxalyl chloride (0.75 g) and a mixture of dimethylamine hydrochloride (1.23 g) and triethylamine (2.04 g) to give 0.37 g of ethyl N,N-dimethyl-2,3-epoxysuccinamate (Compound No. 85) as colorless oil.

MS m/e: 187 (M+).
IR $\nu_{max}^{neat}$ cm$^{-1}$: 1740, 1665.
NMR (CDCl$_3$) $\delta$=1.35 (3H, t, J=9.0 H$_z$), 2.95, 2.99 (6H, s,s), 3.65, 3.83 (2H, d,d, J=2.0 H$_z$), 4.30 (2H, q, J=9.0 H$_z$).

EXAMPLE 55

Following the procedure of Example 53, monoethyl potassium epoxysuccinate (0.99 g) was successively treated with oxalyl chloride (0.75 g) and a mixture of L-proline benzyl ester hydrochloride (1.85 g) and triethylamine (1.5 g) to give 1.35 g of ethyl N-1'-carbobenzoxytetramethylene-2,3-epoxysuccinamate (Compound No. 86) as colorless oil.

MS m/e: 347 (M+).
IR $\nu_{max}^{neat}$ cm$^{-1}$: 1750, 1670.
NMR (CDCl$_3$) $\delta$=1.30 (3H, t, J=9.0 H$_z$), 1.50-2.60 (4H, m), 3.40-4.00 (4H, m), 4.22 (2H, q, J=9.0 H$_z$), 4.63 (1H, m), 5.11 (2H, s), 7.26 (5H, s).

EXAMPLE 56

Following the procedure of Example 53, monoethyl potassium epoxysuccinate (0.99 g) was successively treated with oxalyl chloride (0.75 g) and a mixture of L-proline methyl ester hydrochloride (0.91 g) and triethylamine (1.5 g) to give 0.83 g of ethyl N-1'-carbomethoxytetramethylene-2,3-epoxysuccinamate (Compound No. 87) as colorless oil.

MS m/e: 271 (M+).
IR $\nu_{max}^{neat}$ cm$^{-1}$: 1750, 1650.
NMR (CDCl$_3$) $\delta$=1.32 (3H, t, J=9.0 H$_z$), 1.50-2.63 (4H, m), 3.30-4.10 (4H, m), 3.87 (3H, s), 4.25 (2H, q, J=9.0 H$_z$), 4.63 (1H, m).

EXAMPLE 57

Following the procedure of Example 53, monoethyl potassium epoxysuccinate (0.99 g) was successively treated with oxalyl chloride (0.75 g) and a mixture of L-proline butyl ester hydrochloride (1.14 g) and triethylamine (1.5 g) to give 1.02 g of ethyl N-1'-carbobutoxytetramethylene-2,3-epoxysuccinamate (Compound No. 88) as colorless oil.

MS m/e: 313 (M+).
IR $\nu_{max}^{neat}$ cm$^{-1}$: 1755, 1650.
NMR (CDCl$_3$) $\delta$=0.93 (3H, t, J=9.0 H$_z$), 1.35 (3H, t, J=9.0 H$_z$), 1.49-2.65 (8H, m), 3.32-4.20 (8H, m), 4.60 (1H, m).

Following the procedure of Example 53, there were obtained the following epoxysuccinamic acid compounds:
Isoamyl N-methyl-2,3-epoxysuccinamate (Compound No. 89)
Isoamyl N,N-dimethyl-2,3-epoxysuccinamate (Compound No. 90)
Benzyl N-methyl-2,3-epoxysuccinamate (Compound No. 91)
Ethyl N-1'-carbobenzoxypentamethylene-2,3-epoxysuccinamate (Compound No. 92).

EXAMPLE 58

To a solution of ethyl N-phenyl-2,3-epoxysuccinamate (Compound No. 1) (0.5 g) and isopropanol (1.0 g) in benzene (30 ml), a catalystic amount of a concentrated sulfuric acid was added, the mixture was refluxed for 5 hours. The reaction mixture was washed with a saturated aqueous sodium chloride solution, dried over magnesium sulfate and concentrated to dryness. The residue thus obtained was treated by silica gel column chromatography using benzene as a developer and the resulting crude crystals were recrystallized from a mixture of n-hexane-acetone to give 0.41 g of isopropyl N-phenyl-2,3-epoxysuccinamate (Compound No. 93) as colorless needles melting at 113°-114.5° C.

EXAMPLE 59

Following the procedure of Example 58, there was obtained 0.32 g of cyclohexanemethyl N-phenyl-2,3-epoxysuccinamate (Compound No. 94) as colorless needles melting at 98°-100° C. from phenyl N-phenyl-2,3-epoxysuccinamate (Compound No. 28) (0.34 g) and cyclohexanemethanol (0.35 g).

EXAMPLE 60

Ethyl N-phenyl-2,3-epoxysuccinamate (Compound No. 1) (0.9 g) was dissolved in ethyl alcohol (30 ml) and an ethyl alcohol solution (5 ml) containing KOH (0.27 g) was added to the solution under ice-cooling, followed by stirring for an hour. The precipitate produced was collected on a filter and recrystallized from a mixture of ethyl alcohol-water to give 0.7 g of potassium N-phenyl-2,3-epoxysuccinamate (Compound No. 95) as colorless powder melting over 300° C. (decomposition).

IR $\nu_{max}^{KBr}$ cm$^{-1}$: 3400, 1680, 1610.
NMR (D$_2$O) $\delta$=3.53, 3.64 (2H, d,d, J=2.0 H$_z$), 7.38 (5H, b.s.).

EXAMPLE 61

Following the procedure of Example 60, there was obtained 0.22 g of potassium N-benzyl-2,3-epoxysuccinamate (Compound No. 96) as colorless powder melting over 300° C. (decomposition) from ethyl N-benzyl-2,3-epoxysuccinamate (Compound No. 13) (0.45 g) and KOH (0.1 g).

IR $\nu_{max}^{KBr}$ cm$^{-1}$: 3300, 1650, 1610.
NMR (D$_2$O) $\delta$=3.36, 3.47 (2H, d,d, J=2.0 H$_z$), 4.30 (2H, s), 7.20 (5H, s).

EXAMPLE 62

Following the procedure of Example 60, there was obtained 0.25 g of potassium N-isoamyl-2,3-epoxysuccinamate (Compound No. 97) as colorless powder melting over 300° C. (decomposition) from ethyl N-isoamyl-2,3-epoxysuccinamate (Compound No. 17) (0.5 g) and KOH (0.122 g).

IR $\nu_{max}^{KBr}$ cm$^{-1}$: 3300, 1650, 1610.
NMR (D$_2$O) $\delta$=0.85 (6H, d, J=5.0 H$_z$), 0.90-1.85 (3H, m), 3.20 (2H, t, J=6.0 H$_z$), 3.36 3.47 (2H, d,d, J=2.0 H$_z$).

EXAMPLE 63

Following the procedure of Example 60, there was obtained 0.235 g of potassium N-cyclohexanemethyl-2,3-epoxysuccinamate (Compound No. 98) as colorless powder melting over 300° C. (decomposition) from ethyl N-cyclohexanemethyl-2,3-epoxysuccinamate (Compound No. 20) (0.38 g) and KOH (0.084 g).

IR $\nu_{max}^{KBr}$ cm$^{-1}$: 3300, 1640, 1610.

NMR (D$_2$O) δ=0.90-1.90 (11H, b.s.), 3.02 (2H, d, J=5.0 H$_z$), 3.34, 3.45 (2H, d,d, J=2.0 H$_z$).

EXAMPLE 64

Following the procedure of Example 60, there was obtained 0.168 g of potassium N-1'-carbopotassium oxytetramethylene-2,3-epoxysuccinamate (Compound No. 99) as colorless powder melting over 300° C. (decomposition) from ethyl N-1'-carbobutoxytetramethylene-2,3-epoxysuccinamate (Compound No. 88) (0.347 g) and KOH (0.15 g).

IR $\nu_{max}^{nujol}$ cm$^{-1}$: 1670, 1603

NMR (D$_2$O) δ=1.60-2.50 (4H, m), 3.20-4.00 (4H, m), 4.20-4.70 (1H, m).

EXAMPLE 65

Following the procedure of Example 60, there was obtained 0.24 g of sodium N-cyclohexyl-2,3-epoxysuccinamate (Compound No. 100) as colorless powder melting over 300° C. (decomposition) from ethyl N-cyclohexyl-2,3-epoxysuccinamate (Compound No. 19) (0.5 g) and NaOH (0.087 g).

IR $\nu_{max}^{KBr}$ cm$^{-1}$: 3300, 1650, 1610.

NMR (D$_2$O) δ=0.80-2.10 (10H, b.s.), 3.42, 3.62 (2H, d,d, J=2.0 H$_z$), 3.65 (1H, b.s.).

Following the procedure of Example 60, there were obtained the following epoxysuccinamic acid compounds:

Potassium N-pentamethylene-2,3-epoxysuccinamate (Compound No. 101)

Potassium N-ethyl-2,3-epoxysuccinamate (Compound No. 102)

Sodium N-tetramethylene-2,3-epoxysuccinamate (Compound No. 103)

Sodium N-phenyl-2,3-epoxysuccinamate (Compound No. 104)

EXAMPLE 66

Potassium N-phenyl-2,3-epoxysuccinamate (Compound No. 95) (2.31 g) was dissolved in water (10 ml) and the solution was made acidic by addition of 25% HCOOH under ice-cooling with stirring. The reaction mixture was extracted with chloroform, washed with a saturated aqueous sodium chloride solution, dried over magnesium sulfate and concentrated to dryness. The residue was recrystallized from a mixture of n-hexane-acetone to give 1.52 g of N-phenyl-2,3-epoxysuccinamic acid (Compound No. 105) as colorless needles melting at 124°-128° C.

EXAMPLE 67

Following the procedure of Example 66, there was obtained 53 mg of N-1'-carboxytetramethylene-2,3-epoxysuccinamic acid (Compound No. 106) as colorless needles melting at 155°-160° C. from potassium N-1'-carbopotassiumoxytetramethylene-2,3-epoxysuccinamate (Compound No. 99) (0.1 g).

Following the procedure of Example 66, there were obtained the following epoxysuccinamic acid compounds using the corresponding starting materials, respectively:

N-Cyclohexyl-2,3-epoxysuccinamic acid (Compound No. 107)

N-Cyclopentanemethyl-2,3-epoxysuccinamic acid (Compound No. 108)

What is claimed is:

1. Trans-epoxysuccinamic acid derivatives of the formula:

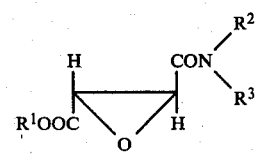

wherein R$^1$ is hydrogen, alkali metal, alkyl having 1-5 carbon atoms, alkenyl having 2-4 carbon atoms, alkynyl having 2-4 carbon atoms, phenyl, benzyl, cycloalkyl having 5-6 carbon atoms, cycloalkenyl having 5-6 carbon atoms, cycloalkenemethyl having 6-7 carbon atoms, or alkyl having 1-3 carbon atoms substituted with cycloalkyl having 5-6 carbon atoms, R$^2$ is hydrogen or alkyl having 1-5 carbon atoms and R$^3$ is phenyl, benzyl, furfuryl, thenyl, pyridyl, quinolinyl, cycloalkanemethyl having 4-7 carbon atoms, or phenyl substituted with 1-3 members selected from the group consisting of halogen, methyl, trifluoromethyl, methoxy, acetyl, hydroxy and nitro, or R$^2$ and R$^3$ taken together with the nitrogen atom to which they are attached form a 5-6 membered heterocyclic ring selected from the group consisting of pyrrolidino, piperidino, piperazino, morpholino and thiamorpholino, or said 5-6 membered heterocyclic ring substituted with methyl.

2. A trans-epoxysuccinamic acid derivative according to claim 1 wherein R$^1$ is alkyl having 1-5 carbon atoms or cycloalkyl having 5-6 carbon atoms, R$^2$ is hydrogen, and R$^3$ is phenyl.

3. A trans-epoxysuccinamic acid derivative in accordance with claim 2 wherein R$^1$ is ethyl.

* * * * *